US006402517B1

United States Patent
Hozumi et al.

(10) Patent No.: US 6,402,517 B1
(45) Date of Patent: Jun. 11, 2002

(54) ARTIFICIAL TOOTH ROOT WITH ANTI-ADHERENCE OF SORDES AND VARIOUS GERMS, WITH ACID RESISTANCE AND ITS PREPARATION METHOD

(75) Inventors: Atsushi Hozumi; Masahiko Inagaki; Kaori Nishizawa; Fukue Nagata; Yoshiyuki Yokogawa; Tetsuya Kameyama, all of Aichi (JP)

(73) Assignee: Agency of Industrial Science and Technology, Tokyo (JP)

( * ) Notice: Subject to any disclaimer, the term of this patent is extended or adjusted under 35 U.S.C. 154(b) by 0 days.

(21) Appl. No.: 09/513,200

(22) Filed: Feb. 25, 2000

(30) Foreign Application Priority Data

Jul. 5, 1999 (JP) .......................................... 11-190163

(51) Int. Cl.[7] ................................................ A61C 8/00
(52) U.S. Cl. .................. 433/201.1; 433/173; 623/23.72
(58) Field of Search .............................. 433/201.1, 172, 433/173, 174, 175, 176; 623/23.72

(56) References Cited

U.S. PATENT DOCUMENTS

| | | | | |
|---|---|---|---|---|
| 4,813,876 A | * | 3/1989 | Wang | 433/224 |
| 4,895,516 A | * | 1/1990 | Hulten | 433/201.1 |
| 5,759,205 A | * | 6/1998 | Valentini | 433/201.1 |
| 6,069,295 A | * | 5/2000 | Leitao | 433/201.1 |

FOREIGN PATENT DOCUMENTS

| | | |
|---|---|---|
| JP | 58-169443 | 10/1983 |
| JP | 62-213750 | 9/1987 |

OTHER PUBLICATIONS

T. Kasuga, et al., Material Integration, vol. 12, No. 5, pp. 27–31, "Novel Castable Ceramic Dental Crowns with Bacteriostatic Activities," 1999.
Kaguka to Kogyo, vol. 46, No. 12, pp. 58–61, 1993.
S. Katayama, et al., J. Jpn Prosthodont Soc, vol. 30, pp. 665–670, Periodontal Evaluation of Abutment Teeth, 1986.

* cited by examiner

*Primary Examiner*—John J. Wilson
(74) *Attorney, Agent, or Firm*—Oblon, Spivak, McClelland, Maier & Neustadt, P.C.

(57) ABSTRACT

The invention provides an artificial tooth root having acid resistance and anti-adherence of sordes and various germs, consisting of a substrate and a coating of calcium phosphate based ceramic having bioaffinity formed on the surface of this substrate, the substrate is composed of a polymer, ceramic, metal, or other material, the surface of the ceramic coating on the substrate surface is endowed with a protrusion-and-recession configuration, and is, chemically modified, and to a method for producing the artificial tooth root, by forming a coating of calcium phosphate based ceramic having bioaffinity over a substrate while imparting protrusions and recessions thereto, masking an area of the ceramic coating surface of which bioaffinity is required, and fixing a silane coupling agent exclusively over a predetermined area of the ceramic coating surface.

1 Claim, 2 Drawing Sheets

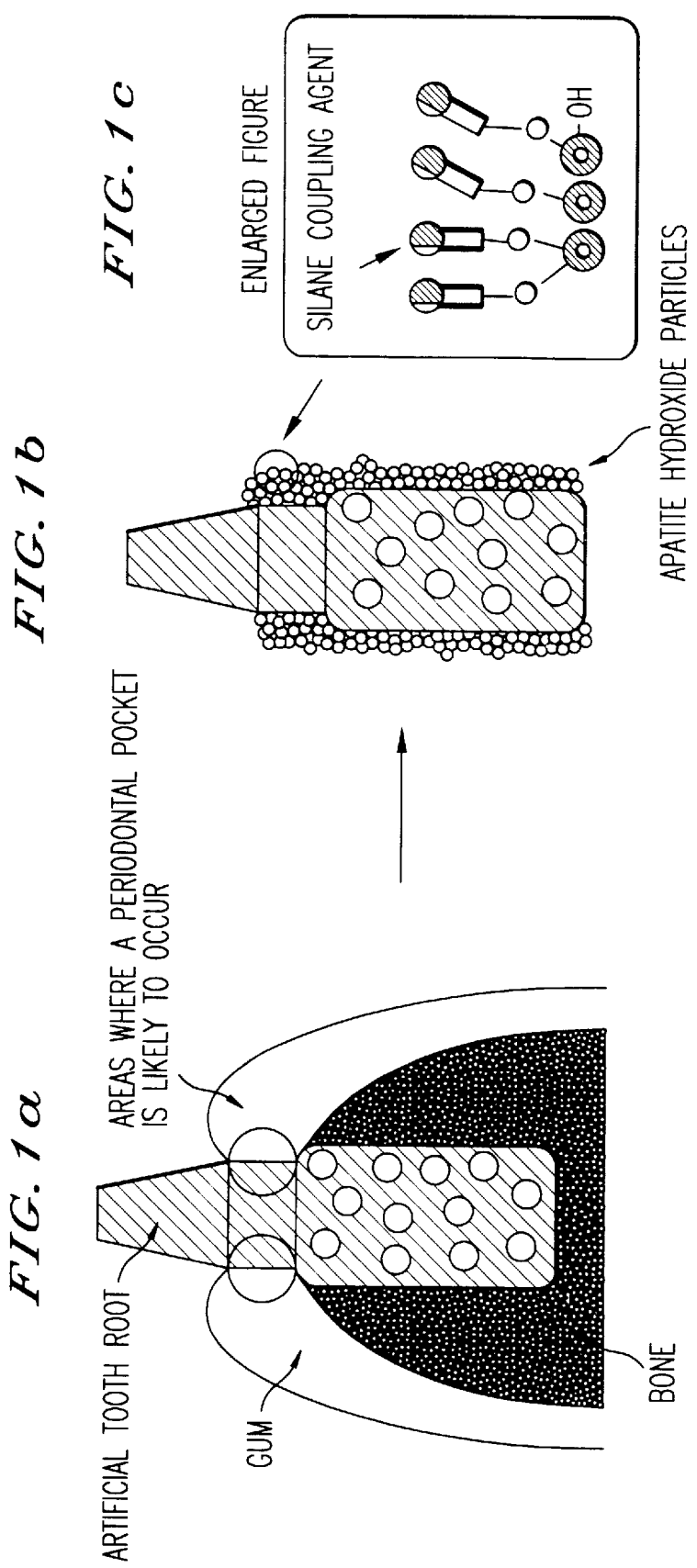

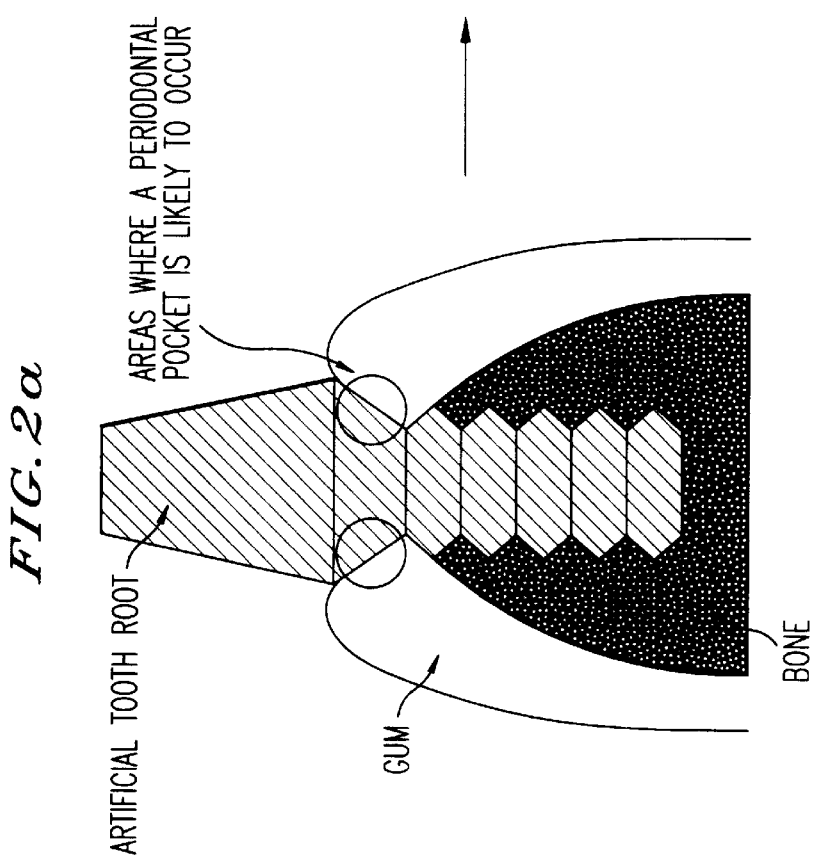
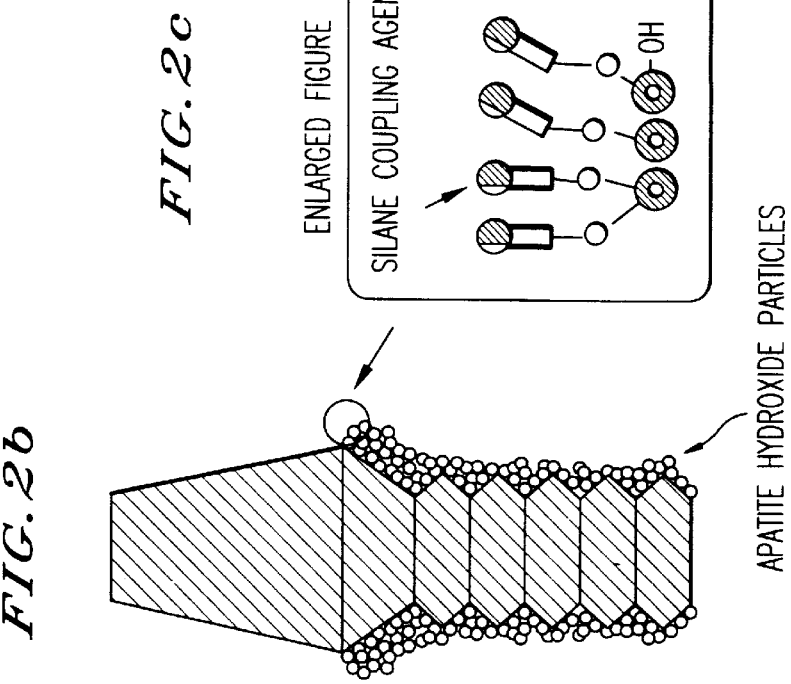
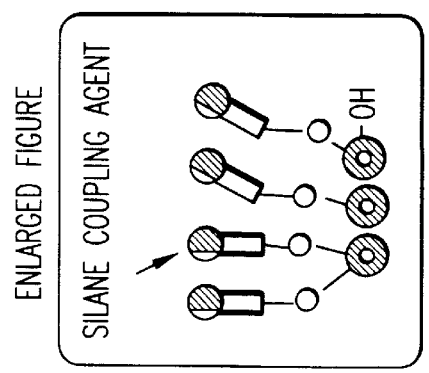

ARTIFICIAL TOOTH ROOT WITH ANTI-ADHERENCE OF SORDES AND VARIOUS GERMS, WITH ACID RESISTANCE AND ITS PREPARATION METHOD

BACKGROUND OF THE INVENTION

1. Field of the Invention

The present invention relates to an artificial tooth root selectively imparted with acid resistance and with anti-adherence of sordes and various germs in areas where a periodontal pocket is likely to occur, and to a production process therefor. More particularly, the invention relates to a novel surface treatment technique for selective surface treatment of a predetermined area of a dentistry material, which can give a properties of anti-adherence of sordes such as tobacco tar and various germs to a predetermined area of the surface of an artificial tooth root coated with calcium phosphate based ceramic having bioaffinity.

2. Description of the Related Art

Periodontal disease and similar disorders stem from infections in the space of tooth and gingival, i.e., periodontal pockets. In many cases, infection recurs due to infiltration of various germs from the area around a repaired tooth or dental crown. Kasuga et al. succeeded in imparting antibacterial properties to the surface of crystalline glass for artificial crowns by introducing silver ions by means of ion exchange (Material Integration (1999), Vol. 12, No. 5, p. 27). The resultant surface exhibits high antibacterial properties against *Escherichia coli* and *Staphylcoccus aureus*.

Yoshino et al, with the aim of preventing adherence of sordes to surfaces of dentistry materials such as dental prostheses, employed a silane coupling agent with a fluorocarbon chain in order to modify the surface of a substrate (Kagaku to Kogyc(1993), Vol. 46, No. 12, p, 58). Depending on the nature of the substrate treated, the resultant surface exhibits water repellence as high as 100 to 115°, reducing adherence of sordes.

Through these methods, it has been possible to control adherence of various germs or contaminant of the dentistry materials. However, the former process, while imparting exceptional antibacterial properties, has no effect whatsoever in terms of inhibiting adherence of sordes. Surfaces treated by the latter process exhibit a water droplet contact angle of around 100 to 115°. However, with a contact angle on this order, there is 30% contact between the surface and a water droplet, so with extended use adherence of sordes occurs, and there is a deterioration of initial performance. Further, the process is decidedly not "environmentally friendly", requiring a large number of processing steps, using copious amounts of water, using organic solvents, etc. Neither of the processes described above is readily adapted to selective surface treatment of a predetermined area.

Calcium phosphate based-ceramics have a number of advantages, such as earlier ossification than do titanium implants, and direct bonding with bone. Clinical application of these materials as dental implants is advancing. However, these ceramics have low strength and tend to be brittle, making use per se as implants difficult. Accordingly, calcium phosphate based ceramics are typically coated onto titanium or a titanium alloy by a plasma spraying process or the like for use. However, differences in the coefficient of thermal expansion between titanium or titanium alloys and the coating film give rise to residual stress, resulting in delamination from the substrate, loss of the film through dissolution of the coating film due to depressed pH in the adjacent area, and other problems; thus, over the long term, titanium implants offer greater reliability. It has been reported by Katayama et al. that depressed pH tends to occur within periodontal pockets, with pH dropping on average to around 6 (Hotei Shi (1986), Vol. 30, p. 665).

With the foregoing in view, thoroughgoing research conducted by the inventors has led to the discovery that introduction of fluorocarbon chains or long-chain alkyl groups to a predetermined area of the surface of a calcium phosphate based ceramic coating produced on a titanium or titanium alloy implant by means of plasma spraying etc., that is, to an area susceptible to formation of a periodontal pocket, appreciably improves water repellence, appreciably reduces adherence of sordes and various germs, and appreciably improves resistance to acid. The present invention was perfected on the basis of this discovery.

Specifically, the present invention provides an artificial tooth root particularly effective as a dentistry material imparted in a predetermined area of the implant with exceptional resistance to adherence of sordes and various germs, as well as with resistance to acid, and offering appreciably reduced dissolution of the calcium phosphate based ceramic in portions thereof exposed within a periodontal pocket. Further provided is a process for the production thereof.

SUMMARY OF THE INVENTION

The present invention provides an artificial tooth root having acid resistance and anti-adherence of sordes and various germs, as well as a process for the production thereof.

The invention relates to an artificial tooth root which is a dentistry material consisting of a substrate and a coating of calcium phosphate based ceramic having bioaffinity formed on the surface of this substrate, the substrate is composed of a polymer, ceramic, metal, or other material, wherein the surface of the ceramic coating on the substrate surface is endowed with a protrusion-and-recession configuration and is chemically modified, and to a production process for the artificial tooth root endowed with acid resistance and with anti-adherence of sordes and various germs, comprising the steps of forming a coating of calcium phosphate based ceramic having bioaffinity over a substrate while imparting protrusions and recessions thereto, masking an area of the ceramic coating surface of which bioaffinity is required by a material, and then fixing a silane coupling agent exclusively over a predetermined area of the ceramic coating surface, namely, an area where a periodontal pocket is likely to occur.

DESCRIPTION OF THE INVENTION

To solve the problems described above, the present invention is composed of the following technical means.

(1) An artificial tooth root with acid resistance and anti-adherence of sordes and various germs, which comprises of a substrate and a coating of calcium phosphate based ceramic having bioaffinity formed on the surface of the substrate, the substrate is composed of a polymer, ceramic, metal, or other material, the surface of the ceramic coating on the substrate surface is endowed with a protrusion-and-recession configuration, and is chemically modified.

(2) The artificial tooth root according to (1) above, wherein the protrusions and recessions provided to the ceramic coating surface have a ridge-to-trough distance of 50 nm or greater.

(3) The artificial tooth root according to (1) above, wherein the silane coupling agent is fixed over a predetermined area of the ceramic coating surface situated in proximity to the boundary of the gum and the dental crown, where is susceptible to bacterial infiltration and to gingivitis.

(4) The artificial tooth root according to (1) above, wherein the silane coupling agent contains a fluorocarbon chain, long-chain alkyl group, or other hydrophobic group.

(5) A method for producing the artificial tooth root with acid resistance and anti-adherence of sordes and various germs as defined in (1) above, comprising the steps of forming a coating of calcium phosphate based ceramic having bioaffinity over a substrate while imparting protrusions and recessions thereto, masking an area of the ceramic coating surface of which bioaffinity is required by a material, and then fixing a silane coupling agent exclusively over a predetermined area of the ceramic coating surface, where a periodontal pocket is likely to occur.

The invention is now described in greater detail.

The most notable feature of the invention resides in the element of producing a coating of calcium phosphate based ceramic having bioaffinity layer over a titanium or titanium alloy substrate by means of a dipping process, electrophoresis, flame spraying process, plasma spraying process, or the like, and fixing by means of a chemical reaction (namely, dehydration/condensation reaction) a silane coupling agent having a hydrophobic group, such as a fluorocarbon chain, long-chain alkyl group, etc., to a predetermined area of the coating layer, namely, an area where a periodontal pocket is likely to occur.

Substrates useable in the present invention include those arbitrarily selected for use from among titanium, titanium alloys, ceramics, polymers, stainless steel, etc. The use of titanium alloys is preferred. As specific examples of substrates, a hollow circular artificial tooth root or a screw type artificial tooth root, for example, may be given by way of example. Examples of calcium phosphate based ceramics having bioaffinity that may be used include inter alia apatite hydroxide, β-tricalcium phosphate (β-TCP), α-TCP, tetracalcium phosphate (TeCP), etc. Formation of the coating layer may be accomplished by any of a number of processes such as dipping, electrophoresis, flame spraying, plasma spraying, etc. In preferred practice, a plasma spraying process is preferred. As regards materials that may be used with plasma Spraying processes, calcium phosphate based ceramic powders may be used. To enhance fixation of the coating layer to the substrate, a mixture of pure titanium powder and calcium phosphate based ceramic powder in any desired ratio may be used. The particle size of tie powder used is not critical, but in preferred practice will be from 0.1 to 300 microns. In preferred practice, to ensure the presence of an air layer in spaces between the protrusion-recession, the protrusions and recessions provided to the surface of the coating layer will have a ridge-to-trough distance of 50 nm or greater. For plasma spraying, an atmospheric pressure plasma spraying process, partial vacuum plasma spraying process, or the like may be used. In preferred practice, an atmospheric pressure plasma spraying process, which permits high temperatures to be produced, will be used. Types of plasma include high frequency plasma, DC plasma, microwave plasma, etc. In preferred practice, high frequency plasma is preferred as there is not risk of contamination of the coating by wear of the electrode material, etc.

Next, the substrate surface on which a layer of calcium phosphate based ceramic having bioaffinity has been formed as noted is cleaned with ultraviolet radiation, ozone, plasma, etc., to remove any organic matter adhering to the surface. Here, the use of short-wavelength vacuum ultraviolet (a 172 nm excimer lamp) is preferred. Next, the dehydration/condensation reaction among hydroxyl groups present on the coating layer surface and hydroxyl groups present in the silane coupling agent having a hydrophobic group, e.g., fluorocarbon chain or long-chat alkyl group, is utilized to bring about secure fixation of these silane coupling agents to the coating layer surface. The fixing method is not critical, but in preferred practice will be a chemical vapor phase surface modification process, which does not require costly reaction equipment, extended treatment times, or the use of organic solvents, and which affords treatment with extremely small amounts of material. Here, in preferred practice, treatment temperature is from 100 to 150° C. and treatment time from 1 to 3 hours.

Bioaffinity is required in areas other than a predetermined area, namely, the area susceptible to formation of a periodontal pocket, so these areas are masked prior to fixing the silane coupling agent. Masking may be accomplished, for example, by applying a polyimide based resin and curing for 2 to 60 minutes at 350 to 400° C. The masking agent is removed with a phenolic stripping agent once the silane coupling agent has become fixed. The area to be masked will differ by individual depending on bone morphology, etc., but in preferred practice will extend 12 mm from the tip of the artificial tooth root. By so doing, the area that will contact the bone (the masked area) is imparted with bioaffinity, thereby promoting ossification, while the area susceptible to formation of a periodontal pocket (the non-masked area is imparted with appreciably acid resistance and antiadherence of sordes and various germs.

In this way, the invention described herein provides selective surface treatment of a predetermined area of an artificial tooth root by means of a simple process.

The reason that predetermined area of the treated substrate exhibits high resistance to adherence of sordes and various germs and resistance to acid is thought to lie in a synergistic effect on the part of chemical effects produced by the fluorocarbon chains or long-chain alkyl groups fixed on the coating layer surface, and physical effects resulting from the presence of protrusions and recessions on the coating layer surface.

BRIEF DESCRIPTION OF THE DRAWINGS

FIG. 1 is a schematic .sectional view of the coating layer pertaining to EXAMPLE 1.

FIG. 2 is a schematic sectional view of the coating layer pertaining to EXAMPLE 2.

BEST MODE FOR CARRYING OUT THE INVENTION

The invention is described in detail through the following examples, which are merely illustrative of the invention and should not be construed as limiting of the invention.

EXAMPLE 1

As calcium phosphate based powder, apatite hydroxide powder of 1-micron particle size was introduced into a 12.56 MHz high-frequency plasma generated by applying voltage of 12 kW, and was subjected to direct plasma spraying onto a hollow cylindrical artificial tooth root of titanium alloy to produce a coating layer about 50 microns in thickness. The protrusions and recessions of the coating surface had a ridge-to-trough distance of about 300 nm. The surface was irradiated for about 10 minutes with an excimer lamp to effect photocleaning. The portion of the artificial tooth root to contact bone was then masked with polyimide based resin, and was held for 3 hours in a 150° C. electric oven together with vapor of a silane coupling agent containing a fluorocarbon chain (KBM7803, manufactured by Shnetsu Ragaku). The masking was then removed with a phenolic stripping liquid. The treated specimen exhibited a water droplet contact angle of about 155°. The specimen was immersed in a pH 6 solution (adjusted by adding acetic acid and a buffer to a 0.9% NaCl solution) maintained at about 37.5° C. for 200 days. After 200 days, cumulative $Ca^{2+}$ elation topped out at approximately 4.58 $mg/cm^3$, about 0.15% of the coating layer.

EXAMPLE 2

As calcium phosphate based powder, apatite hydroxide powder of 5-micron particle size was introduced into a 12.56 MHz high-frequency plasma generated by applying voltage of 12 kW, and was subjected to direct plasma spraying onto a screw type artificial tooth root of titanium alloy to produce a coating layer about 50 microns in thickness. The protrusions and recessions of the coating surface had a ridge-to-trough distance of about 700 nm. The surface was irradiated for about 10 minutes with an excimer lamp to effect photocleaning. The portion of the artificial tooth root to contact bone was then masked with polyimide based resin, and was held for 3 hours in a 150° C. electric oven together with vapor of a silane coupling agent containing a long-chain alkyl group (n-octadecyl trimethoxysilane, manufactured by Tokyo Kasei Kogyo). The masking was then removed with a phenolic stripping liquid. The treated specimen exhibited a water droplet contact angle of about 145°. The specimen was immersed in a pH 6 solution (adjusted by adding acetic acid and a buffer to a 0.9% NaCl solution) maintained at about 37.5° C. for 200 days. After 200 days, cumulative $Ca^{2+}$ elution was approximately 7.64 $mg/cm^3$, about 0:24% of the coating layer.

COMPARISON 1

As calcium phosphate based powder, apatite hydroxide powder of 1-micron particle size was introduced into a 12.56 MHz high-frequency plasma generated by applying voltage of 12 kW, and was subjected to direct plasma Spraying onto a hollow cylindrical artificial tooth root of titanium alloy to produce a coating layer about 50 microns in thickness. The protrusions and recessions of the coating surface had a ridge-to-trough distance of about 300 nm. The treated specimen was immersed in a pH 6 solution (adjusted by adding acetic acid and a buffer to a 0.9% NaCl solution) maintained at about 37.5° C. for 200 days.

After 200 days, cumulative $Ca^{2+}$ elution was approximately 63.7 $mg/cm^3$, about 2.01% of the coating layer.

COMPARISON 2

As calcium phosphate based powder, β-tricalcium phosphate powder of 5-micron particle size was introduced into a 12.56 MHz high-frequency plasma generated by applying voltage of 12 kW, and was subjected to direct plasma spraying onto a screw type artificial dental root of titanium alloy. The product was quenched and subjected to hydrothermal synthesis to produce a coating layer about 70 microns in thickness. The protrusions and recessions of the coating surface had a ridge-to-trough distance of about 400 nm. The treated specimen was immersed in a pH 6 solution (adjusted by adding acetic acid and a buffer to a 0.9% NaCl solution) maintained at about 37.5° C. for 200 days. After 200 days, cumulative $Ca^{2+}$ elution was approximately 23.6 $mg/cm^3$, about 0.75% of the coating layer.

The invention described in detail herein relates to an artificial tooth root which is a dentistry material consisting of a substrate and a coating of calcium phosphate based ceramic having bioaffinity formed on the surface of this substrate, wherein the surface of the ceramic coating on the substrate surface is endowed with a protrusion-and-recession configuration and is chemically modified, regardless of whether the substrate is a polymer, ceramic, metal, or other material; and to a production process therefor, whereby the invention offers inter alia the following advantages: 1) provides an artificial tooth root having acid resistance and anti-adherence of sordes and various germs; 2) provides dentistry materials having appreciably reduced dissolution of calcium phosphate based ceramic exposed within a periodontal pocket; 3) provides an artificial tooth root with bioaffinity having exceptional anti-adherence of sordes and various germs, as well as resistance to acid; and 4) affords selective surface treatment of predetermined areas of dentistry materials.

What is claimed is:

1. A method for producing an artificial tooth root with acid resistance and anti-adherence of contaminants and various germs, comprising a substrate and a coating of calcium phosphate based ceramic having bioaffinity formed on the surface of the substrate, wherein the substrate is composed of a polymer, ceramic, metal, or other material, the surface of the ceramic coating on the substrate surface is endowed with a protrusion-and-recession configuration, and a predetermined area of the ceramic coating surface, where a periodontal pocket is likely to occur, is chemically modified by a silane coupling agent, said method comprising the steps of
forming a coating of calcium phosphate based ceramic having bioaffinity over the substrate while imparting protrusions and recessions thereto,
masking an area of the ceramic coating surface of which bioaffinity is required by a material,
and then fixing the silane coupling agent exclusively over a predetermined area of the ceramic coating surface, where a periodontal pocket is likely to occur.

* * * * *